United States Patent
Fang et al.

(10) Patent No.: US 8,753,119 B2
(45) Date of Patent: Jun. 17, 2014

(54) MOUNTING METHOD OF DENTAL CAST

(75) Inventors: Jing-Jing Fang, Tainan (TW); Tung-Yiu Wong, Tainan (TW); Chia-Chang Tsai, Changhua County (TW); Tai-Hong Kuo, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/543,219

(22) Filed: Jul. 6, 2012

(65) Prior Publication Data

US 2013/0011808 A1 Jan. 10, 2013

(30) Foreign Application Priority Data

Jul. 6, 2011 (TW) .............................. 100123947 A (51) Int. Cl.
*A61C 11/00* (2006.01)
*A61C 5/00* (2006.01)

(52) U.S. Cl.
USPC ................ 433/213; 433/54; 433/55; 433/215

(58) Field of Classification Search
USPC .................. 433/54–69, 213–215, 34, 37–38; 382/154, 128, 293, 294; 700/118, 700/97–98; 378/38, 168, 191
See application file for complete search history.

(56) References Cited

U.S. PATENT DOCUMENTS

| 4,014,097 A * | 3/1977 | Pameijer ........................ 433/27 |
| 4,354,836 A * | 10/1982 | Santoni .......................... 433/43 |
| 6,120,290 A * | 9/2000 | Fukushima et al. ............ 433/69 |
| 2009/0179986 A1 * | 7/2009 | Klett ............................... 348/77 |
| 2010/0075274 A1 * | 3/2010 | Klett ............................... 433/56 |

* cited by examiner

*Primary Examiner* — Yogesh Patel
(74) *Attorney, Agent, or Firm* — Muncy, Geissler, Olds & Lowe, P.C.

(57) ABSTRACT

A mounting method of dental cast is disclosed. The mounting method includes the steps of providing an articulator and a label module having at least a label and at least a reference object, generating a label coordinate information in accordance with the reference object and the label, providing a midface and mandible image information and generating a landmark coordinate information in accordance with a plurality of landmarks of the midface and mandible image information, generating a structure coordinate information in accordance with a plurality of structures of the articulator and the label, disposing a first dental cast connected with the label module on the articulator, and providing a detecting device to detect the label and adjust the position of the first dental cast in accordance with the midface and mandible image information, the label coordinate information, and the structure coordinate information.

10 Claims, 10 Drawing Sheets

MOUNTING METHOD OF DENTAL CAST

CROSS REFERENCE TO RELATED APPLICATIONS

This Non-provisional application claims priority under 35 U.S.C. §119(a) on Patent Application No(s). 100123947 filed in Taiwan, Republic of China on Jul. 6, 2011, the entire contents of which are hereby incorporated by reference.

BACKGROUND OF THE INVENTION

1. Field of Invention

The invention relates to a mounting method of dental cast and, in particular, to a mounting method of dental cast with sensing technology assistance.

2. Related Art

Clinically, there are many patients having special maxillofacial ratios or incorrect occlusal relationships between upper and lower jaws. Such a kind of abnormally growth problem often accompanies with the facial asymmetry, the mandibular prognathism, the mandible retrusion or the poor occlusal condition on the organization structure. Regarding the life, the patient tends to encounter the stoppages, such as the pronunciation difficulties, the chewing digestive diseases, the lack of confidence, or even the other's discrimination and the people's strange looks.

Orthodontics is one of the developed therapeutic methods to solve the above problems. In general, during the first consultation, it is necessary to collect the growing record of the patient, make the dental plaster model, inspect the mouth by X-ray, and take the photos of the face and teeth for drafting the proper treatment plan. Then, the removable and fixed orthodontic treatments are applied in sequence according to the treatment plan. In this procedure, the drafted treatment plan is one of the factors of the orthodontics result. Of course, if the drafted treatment plan can not exactly indicate the occlusal relationship of the patient or have some errors, the following orthodontics procedure can be sufficiently affected. Regarding to the above problems, when the situation of the patient is too worse to be treated by orthodontics, it still exists another general and effective treatment, which is to correct the spatial positions of the maxilla and mandible through the surgery and to reconstruct the good occlusal relationship. This kind of surgery is typically referred to as an orthognathic surgery. Similarly, because the object of the orthognathic surgery is to correct the upper facial structure of the jaw, such as the facial asymmetry, the facial harmonious proportion or the like, as well as the growth problem, or to correct the skeleton structure change, which cannot be easily or cannot be completed using braces. So, the detailed preoperative diagnosis has to be made such that the orthognathic surgery planning can be established in connection with the actual situation of the patient's maxillofacial skeleton structure, and the jawbone can be indeed moved to the proper position. Thus, this is referred to as the "orthognathic surgical planning", "orthognathic planning" or "orthognathic surgery planning", the quality of which significantly affects the quality of the surgical behavior.

The orthognathic plan is drafted based on the good symmetry of the dentition and facial jawbone, so that the oral surgery plan can be performed according to the facial characteristics and the occlusal relationship. However, the drafting of the orthognathic plan still encounters many important issues. As mentioned above, either the orthodontics or the orthognathic surgery needs an additional device for transferring the relative relationship between the dentitions, maxilla and mandible, so that the operator or doctor is able to draft a precise surgery plan for the patient. The conventional method is to use a face bow to transfer the relative relationship to an articulator, and then utilize the cephalometric analysis to draft the orthodontic plan or orthognathic plan.

The articulator can match the jawbone characteristics of the patient, such as condyle and Frankfurt horizontal plane (FH plane). The face bow can record the relative relationship of the maxilla and mandible, so that the dental cast of the patient can be precisely fixed on the articulator. Thus, the articulator can exactly reproduce the relationship of jawbone of the patient. This action of positioning and fixing the dental cast on the articulator by the face bow is a mounting step.

However, after the long term experience, it has been proved that the incorrect record of the face bow always results the mounting error, which is one of the major factors causing the unsatisfied orthodontic result with respect to the desired orthodontic plan. Accordingly, various kinds of modified face bows are disclosed to improve the existing problem, but they still have the following drawbacks. First, the included angle between the FH plane and the occlusive surface may be mismatch with each other. This is because the FH plane may not be kept in horizontal when mounting the palate dental cast on the conventional articulator even in the same case in different times. Unfortunately, the mounting of the face bow never considers this undesired event. Second, different postures of the patient may result in different positions of the mandible. According to some researches, when the patient changes his/her posture, such as standing or sitting, the position of mandible can not stay at a fixed position, resulting in undesired error. Third, since the position of the rotation axis of lower jaw, the condyle axis, is a predicted result average measuring from skin, it is possible to cause the error on the third reference point.

Because the convention method to mount the dental cast of the patient on the articulator by the face bow still has some drawbacks, the relative relationship of the dental cast and the articulator may not exactly represent the actual situation. This may increase the mistakes during the orthodontics or orthognathic surgery, or limit the effect of the treatment. Therefore, it is an important subject of the present invention to provide a novel mounting method that can be performed without using the face bow so as to decrease the possible mechanical errors. Moreover, the mounting method of the invention can provide, for example, the 3D visualization and/or quantified data to guide or assist the operator/doctor, thereby decreasing the blind spots of the mounting process so as to exactly transfer the situation of the facial jawbone to the articulator, so that the goal of increasing the success rate of orthodontics and orthognathic surgery can be achieved.

SUMMARY OF THE INVENTION

In view of the foregoing subject, an objective of the present invention is to provide a mounting method of dental cast that can overcome the drawbacks of the conventional method by using the face bow to mount the dental cast on the articulator, thereby exactly representing the actual situation by the relative relationship of the dental cast on the articulator after transferring, and thus to decrease the mistakes during the orthodontics or orthognathic surgery, and improve the effect of the treatment.

The present invention discloses a novel mounting method of dental cast that can be performed without using the conventional face bow so as to decrease the possible mechanical errors. Moreover, the mounting method of the invention provides, for example, the 3D visualization and/or quantified data to guide or assist the operator/doctor, thereby decreasing the blind spots of the mounting process so as to exactly transfer the situation of the facial jawbone to the articulator, so that the possible errors existed before the orthodontic or orthognathic planning can be avoided.

To achieve the above objective, the present invention discloses a mounting method of dental cast. The mounting method includes the steps of: providing an articulator and a label module having at least a label and at least a reference object; generating a label coordinate information in accordance with the reference object and the label; providing a midface and mandible image information and generating a landmark coordinate information in accordance with a plurality of landmarks of the midface and mandible image information; generating a structure coordinate information in accordance with a plurality of structures of the articulator and the label; disposing a first dental cast connected with the label module on the articulator; and providing a detecting device to detect the label and adjust the position of the first dental cast in accordance with the midface and mandible image information, the label coordinate information, and the structure coordinate information.

In one embodiment of the invention, the landmarks comprise condyle, upper edge of auditory meatus, lower edges of orbital bones and/or the reference objects.

In one embodiment of the invention, the structures comprise an upper arm portion, a pivot axis and/or two position indicators of the articulator. Preferably, the structures comprise a center of the pivot axis.

In one embodiment of the invention, the step of generating the structure coordinate information is to detect the structures and the label by the detecting device.

In one embodiment of the invention, the first dental cast is a mandible dental cast.

In one embodiment of the invention, the mounting method further comprises the steps of: providing a second dental cast, wherein the label is disposed between the first dental cast and the second dental cast; and adjusting the position of the second dental cast in accordance with the midface and mandible image information, the label coordinate information, and the structure coordinate information. Preferably, the second dental cast is a palate dental cast.

In one embodiment of the invention, the label module has a bite member, a positioning aid and a label carrying member, the positioning aid has the reference object, two ends of the positioning aid are connected with the bite member and the label carrying member, respectively, and the label is fixed to the label carrying member.

In one embodiment of the invention, the reference object does substantially not generate scattered light under X-ray photograph.

In one embodiment of the invention, the detecting device is an optical, mechanical, ultrasonic, gyroscope or magnetic inductive detecting device.

In one embodiment of the invention, the detecting device is an optical detecting device and comprises two photographing modules, and the label is a light-emitting diode (LED), a pattern or a reflective member.

As mentioned above, the mounting method of dental cast of the invention generates the label coordinate information, the landmark coordinate information, and the structure coordinate information for transferring the detecting results into images. Thus, when the detecting device detects the label to trace the position variations of the dental cast with respect to the articulator, it is possible to present the three-dimensional image model of facial jawbone by using the data processing device to combine the generated information with the midface and mandible image data. Accordingly, the operator or doctor can view the three-dimensional image model to avoid the blind spots. Moreover, the mounting method of the invention can quantify the relationship of special coordinates between the dental cast and the articulator, which can be simply applied to auxiliary calculating software for providing the necessary reference information. Furthermore, since the relative relationship between all objects is determined, it is possible to label the correct mounting location in the image, which is used as the direction and distance references for moving the dental cast. This feature can achieve the desired effect of real-time adjustment.

Compared with the conventional art, the mounting method of dental cast of the invention utilizes the detecting technology to replace the conventional face bow, so that it is possible to trace the difference between the relative relationship of the dental cast and the articulator and the real situation of the patient in real time. Thus, the invention is advantageous in data quantification. Besides, the established image can rapidly and precisely guide the operator or doctor to dispose the dental cast on the proper location. As a result, the present invention can efficiently enhance the reliability of the orthodontics and orthognathic planning.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

The mounting method of dental cast of the invention is applied with a hardware structure containing a detecting device. In order to illustrate the embodiment of the invention in more detailed, the hardware structure and related technical features will be described in advance.

Figure 1A:
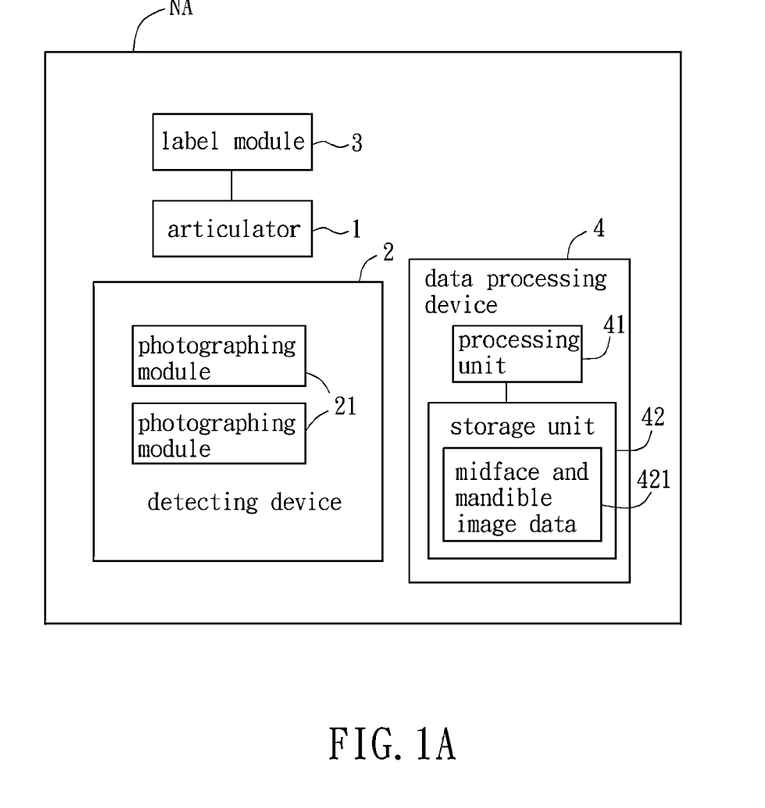
FIG. 1A is a system block diagram showing a planning system in accordance with an embodiment of the invention.
Figure 1B:
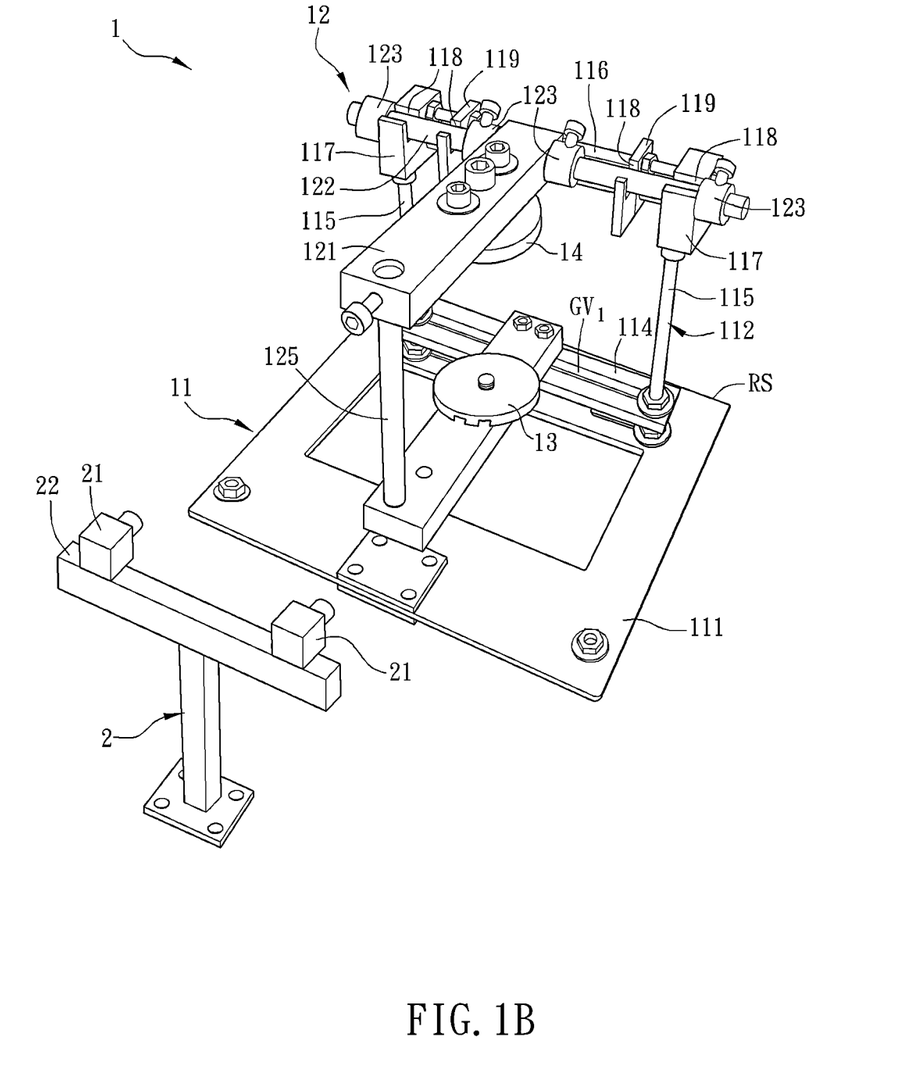
FIG. 1B is a schematic illustration showing an exterior of the planning system of FIG. 1A.

In this embodiment, the mounting method of dental cast is performed by a planning system NA. FIG. 1A is a system block diagram showing the planning system in accordance with an embodiment of the invention, and FIG. 1B is a schematic illustration showing an exterior of the planning system of FIG. 1A. Referring to FIG. 1A, the planning system NA is, for example, an orthodontic planning system or an orthognathic planning system, which includes an articulator 1, a detecting device 2, at least a label module 3 and a data processing device 4. The planning system NA is applied with at least a first dental cast (not shown). Preferably, the first dental cast is a mandible dental cast.

As shown in FIG. 1B, the type of the detecting device 2 is not particularly restricted as long as it can detect or sense the label module 3. For example, the detecting device 2 may be an optical, mechanical, ultrasonic, gyroscope or magnetic inductive detecting device. Of course, different types of detecting devices should work in conjunction with different types of label modules 3. In this embodiment to be described, the detecting device 2 works in conjunction with the active optical technique and has two photographing modules 21, wherein the two photographing modules 21 are disposed on a support structure 22 of the detecting device 2. Preferably, the photographing modules 21 may include, for example but without limitation to, cameras with infrared photographing functions, and the photographing modules 21 have been calibrated and obtained and adjusted the internal parameters and the external parameters. The calibrated photographing module 21 can be used to calculate the stereoscopic visual depth and thus obtains the spatial positioning information of the to-be-tested object. The calibration operation can be easily understood by those skilled in the art and thus will not be described in detail. Although the support structure 22 of this embodiment has the T-shaped frame, it may also have any other arbitrary shape as long as it can fix and maintain the photographing module 21 at the specific position.

Figure 2A:
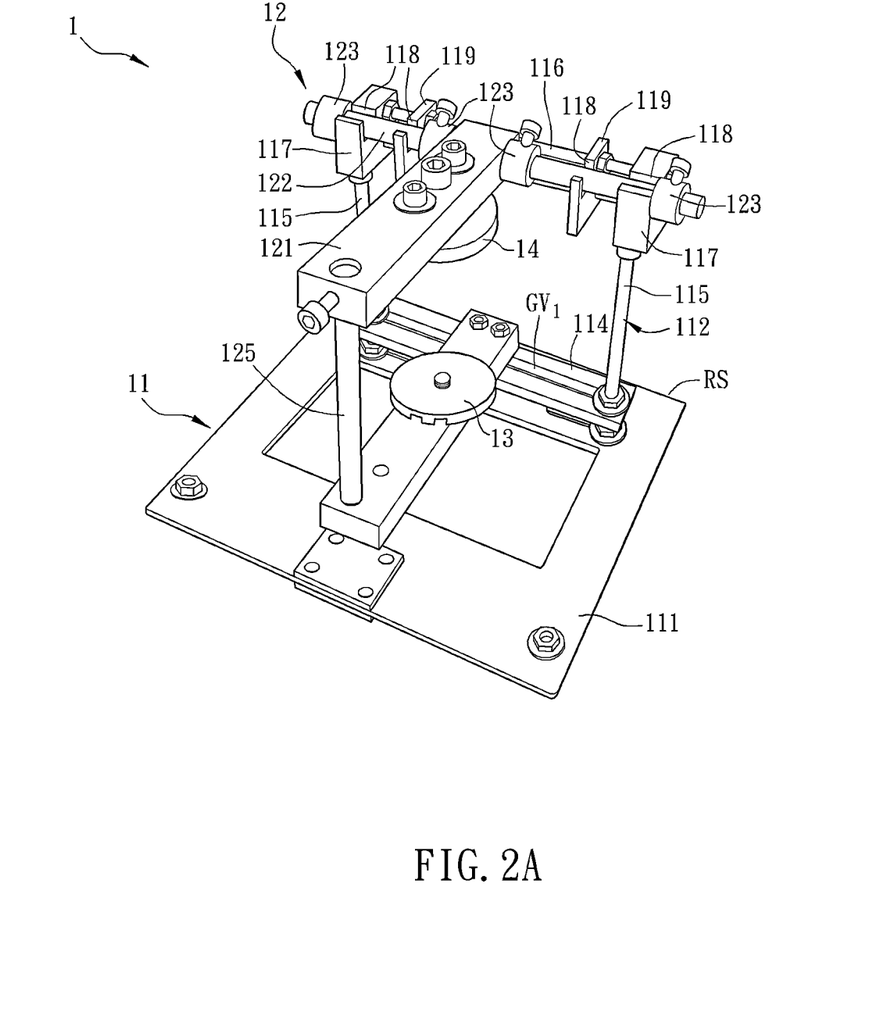
FIG. 2A is a schematic illustration showing an exterior of an articulator in accordance with the embodiment of the invention.
Figure 2B:
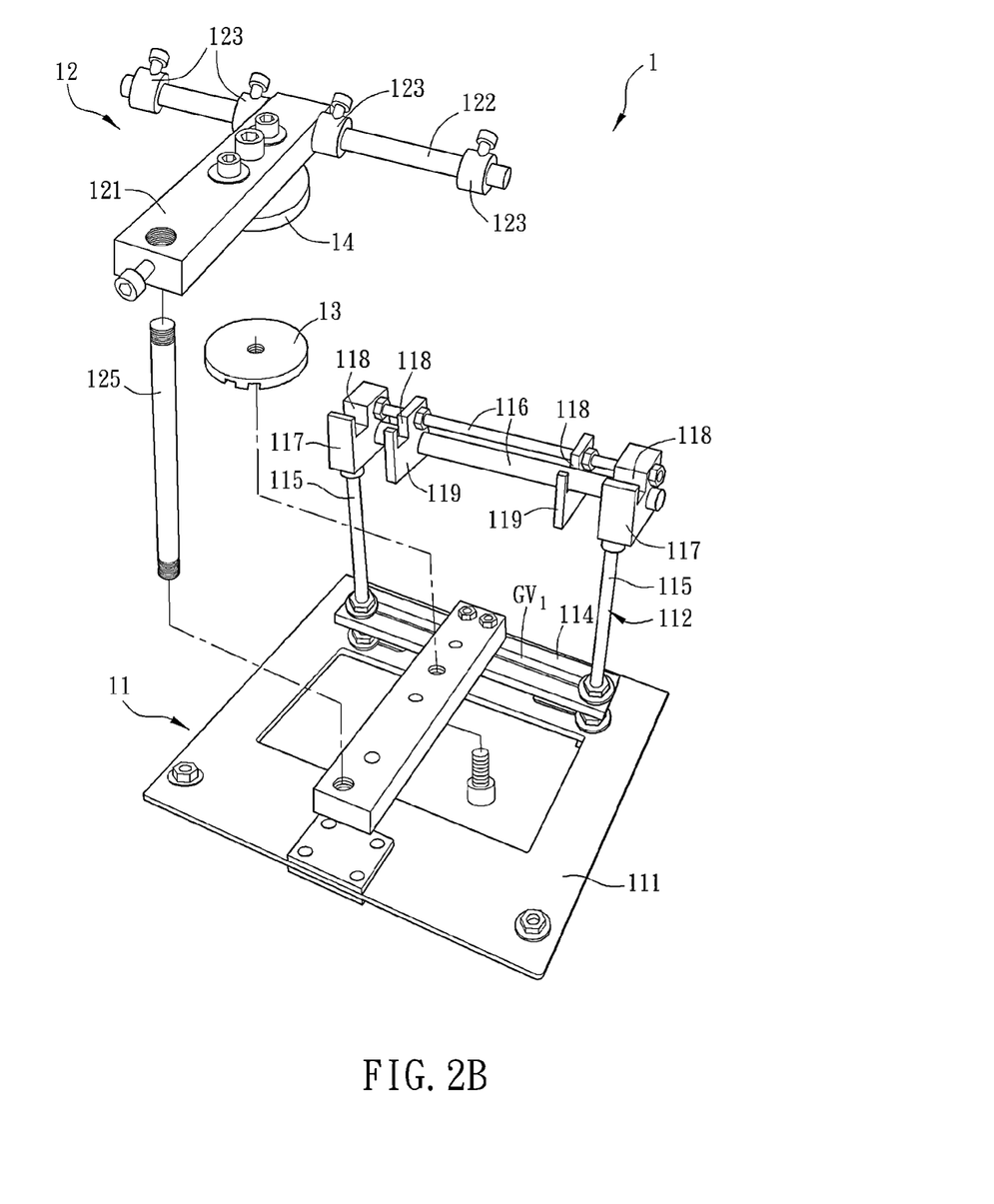
FIG. 2B is an exploded schematic illustration showing the articulator of FIG. 2A.

The detecting device 2 is disposed in correspondence with the articulator 1. The articulator 1 of this invention has the structure, which is not particularly restricted, and may be the typical general or conventional articulator. Of course, the articulator 1 may be a high-level articulator, which is configured with the adjustment mechanism at two sides of the pivot axis. This high-level articulator can be adjusted with respect to the moving mandible, especially to the dynamic occlusion. Since the above-mentioned articulators are all familiar to those skilled in the art, the descriptions thereof are omitted. Besides, the mounting method of dental cast of the invention may also utilize other articulators with the specific structure to be introduced hereinbelow. FIG. 2A is a schematic illustration showing an exterior of an articulator in accordance with the embodiment of the invention, and FIG. 2B is an exploded schematic illustration showing the articulator of FIG. 2A. Referring to FIGS. 2A and 2B concurrently, the articulator 1 of this embodiment has a lower member 11 and an upper member 12, which is detachably mounted on the lower member 11.

In the following, the detailed structures of the lower member 11 and the upper member 12 will be further described.

Figure 3A:
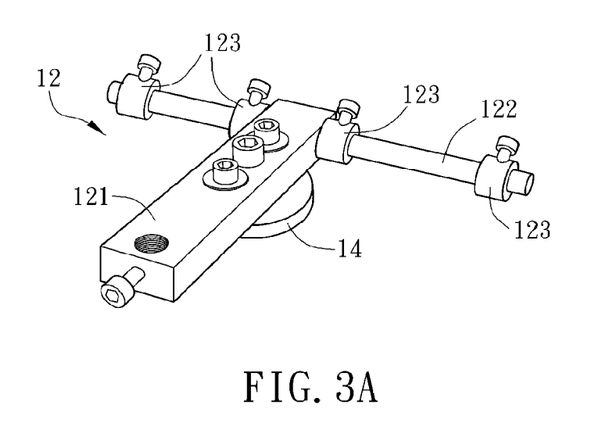
FIG. 3A is a schematic illustration showing the exterior of the upper member of FIG. 2A.
Figure 3B:
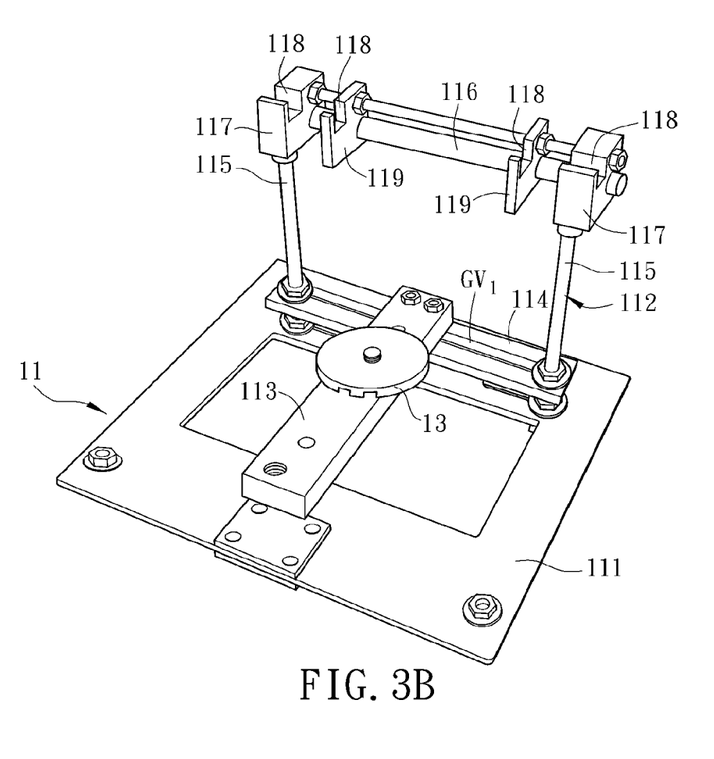
FIG. 3B is a schematic enlarged illustration showing the exterior of the lower member of FIG. 2A.

FIG. 3B is a schematic illustration showing the exterior of the lower member of FIG. 2A. Referring to FIG. 3B, the lower member 11 of this embodiment has a base body 111, a frame structure 112 and a lower arm portion 113. The material of each assembly of the lower member 11 may include, for example but without limitation to, metal, and preferably includes aluminum alloy, wherein the assemblies have the corresponding screw holes so that they can be fixed and connected together by way of screwing. In this embodiment, the lower arm portion 113 is slidingly disposed on the base body 111. In detail, the rear side RS of the base body 111 may have a fixing platen 114 having a lower arm portion groove $GV_1$, and one end of the lower arm portion 113 is slidably disposed thereon. Of course, the lower arm portion groove $GV_1$ may penetrate through the base body, or may be an opening formed on only one side of the base body, and this does not intend to restrict the invention.

The frame structure 112 stands on the rear side RS of the base body 111, and may be further divided into two support columns 115 and two fixing rods 116. In this embodiment, the support column 115 of the frame structure 112 penetrates through two ends of the lower arm portion groove $GV_1$ and is vertically fixed to the base body 111, and one end of each support column 115 corresponding to the base body 111 has an upper fixing member 117. The upper fixing member 117 has a slot 118 having, for example, a U-shape to engage with the upper member 12 and provide the support. The two fixing rods 116 correspond to each other vertically, are disposed between the two upper fixing members 117, and may be fixedly disposed in a condition of, for example but without limitation to, penetrating through the two upper fixing members 117. In addition, in other aspects of this embodiment, the frame structure 112 may also have only one fixing rod 116 disposed between the two upper fixing members 117.

The articulator may have, for example but without limitation to, two position indicators 119 movably disposed on two sides of the frame structure 112 of the lower member 11. Preferably, the position indicators 119 indicate the corresponding relative position relationship between the inner sides of the left and right condyles of the patient, and may be additionally referred to as condyle indicators or inner condyle indicators. For the detailed structures, the position indicator 119 is disposed between the two upper fixing members 117. The position indicator 119 may be a plate-like member having a hole through which the fixing rod 116 passes. Similar to the upper fixing member 117, the position indicator 119 may also have the U-shaped slot 118 for supporting the upper member 12. Of course, the two position indicators 119 are not restricted to be moved concurrently. For example, only one position indicator 119 disposed on one side is movable, and the other position indicator 119 disposed on the other side is fixed and the position of the other position indicator 119 cannot be adjusted.

FIG. 3A is a schematic illustration showing the exterior of the upper member of FIG. 2A. Referring to FIG. 3A, the upper member 12 has an upper arm portion 121 and a pivot shaft 122 connected with one end of the upper arm portion 121. Preferably, as shown in the drawing, the pivot shaft 122 is connected with the upper arm portion 121 in a manner penetrating through one end of the upper arm portion 121. Preferably, the pivot shaft 122 and the upper arm portion 121 are substantially located on the same plane and correspond to the Frankfurt horizontal plane (hereinafter referred to as the FH plane) of the patient. The pivot shaft 122 may be a solid cylinder rotatably mounted on the frame structure 112 of the lower member 11. Specifically, it has the shape and the inner diameter matching with the slot 118 of the upper fixing member 117, so that it can be indeed engaged with the upper fixing member 117 without being arbitrarily rotated under the over interference. The assemblies of the upper member 12 may be made of metal, and are preferably made of aluminum alloy, and are fixed together by way of screwing.

Referring to again to FIG. 3B, a plurality of positioning members 123 may be fit with the pivot shaft 122 to fix the relative positions between the upper arm portion 121, the pivot shaft 122 and/or the frame structure 112, respectively. In addition, the articulator may also have a rod-like fixing member 125, which has one end connected with the upper arm portion 121 and the other end connected with the lower arm portion 113.

The articulator is used for accommodating the dental cast of the patient or the person requiring the orthodontics and orthognathic surgery, so a lower alignment member 13 and an upper alignment member 14 corresponding to each other are disposed on the lower arm portion 113 and the upper arm portion 121 of the articulator. In the practical application of this embodiment, the lower alignment member 13 and the upper alignment member 14 may be firstly embedded into the back sides of the mandible and palate dental casts (not shown) corresponding to the teeth occlusal surface, and then the fixing screws are provided to firmly fix the lower alignment member 13 and the upper alignment member 14 to the corresponding surfaces of the lower arm portion 113 and the upper arm portion 121. However, the invention does not intend to restrict the necessity of disposing the dental casts through the lower alignment member 13 and the upper alignment member 14, or the necessity of disposing the lower alignment member 13 and the upper alignment member 14 using the above-mentioned means or order.

Figure 3C:
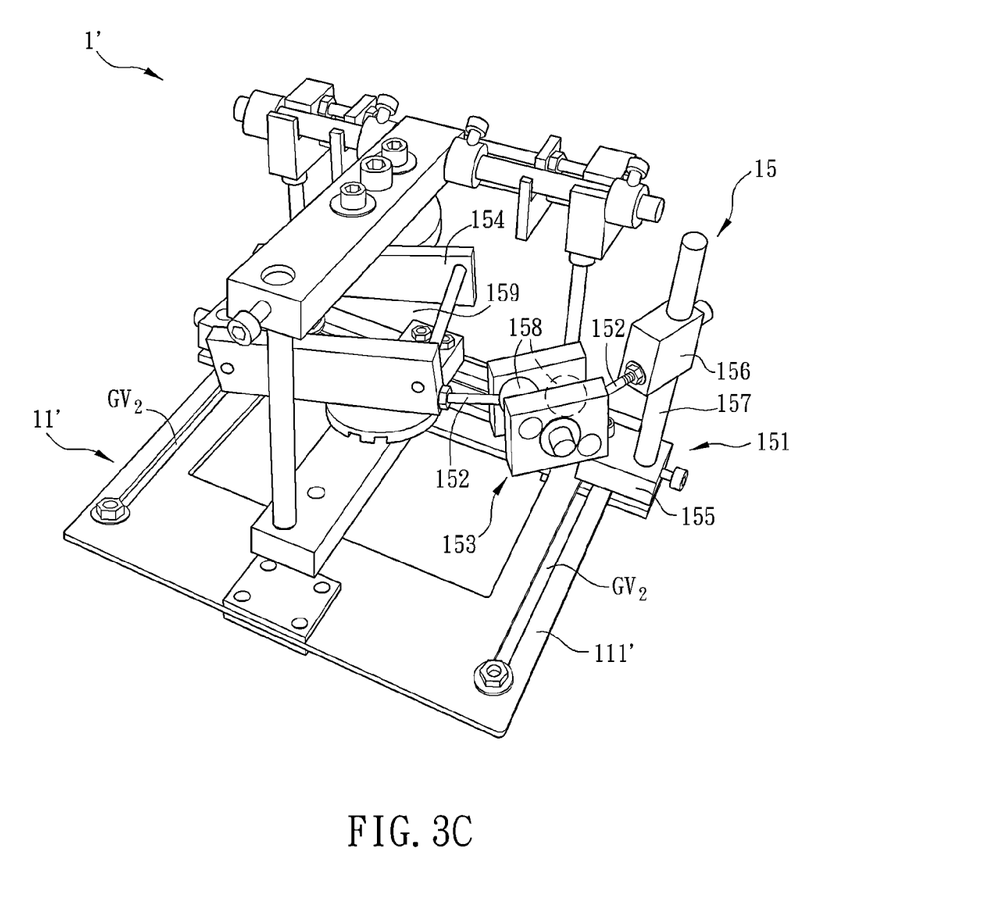
FIG. 3C is a schematic illustration showing the exterior of an articulator in accordance with a modified aspect of the embodiment of the invention.

In addition, when the operator or doctor is cutting and moving the dental cast on the articulator, the material such as the soft wax is required to provide the auxiliary fixing, thereby requiring the repeated softening and fixing steps, and having the poor economic effectiveness in operation. Thus, in addition to the above-mentioned advantages, the articulator of the invention in this aspect is also adapted to the working in conjunction with any structure whose orientation or position can be adjusted, such as a universal arm, especially a hydraulic oil universal arm, so that the above-mentioned problems can be solved. However, it is to be specified that the articulator of the invention may also work in conjunction with a novel approach to serve as another means for solving the similar problems. The approach will be described in the following. However, it is to be emphasized that the novel structure does not intend to restrict the invention. FIG. 3C is a schematic illustration showing the exterior of an articulator in accordance with a modified aspect of the embodiment of the invention. As shown in FIG. 3C, the articulator 1' in this aspect of the embodiment also has elements and the structures of the articulator shown in FIG. 2B, and each of two sides of the base body 111' of the lower member 11' of the articulator 1' further has a dental-cast-adjustment-structure sliding track $GV_2$ for a dental cast adjusting structure 15 to be slidably disposed.

For the detailed structures, the dental cast adjusting structure 15 may have a sliding assembly 151, two links 152, a joint assembly 153 and a dental cast resting assembly 154. The sliding assembly 151 has two block assemblies 155 and 156 and a rod assembly 157, wherein the block assembly 155 is slidingly connected with the dental-cast-adjustment-structure sliding track $GV_2$, and the block assembly 156 is connected with the block assembly 155 in a slidable manner on the rod assembly 157. A dual-sphere joint mechanism mainly constituted by two spheres 158 are disposed on the joint assembly 153, and can provide the rotation in six degrees of freedom. The dental cast resting assembly 154 may be a metal frame having a receptacle 159 for accommodating the dental casts by vertically resting against the dental casts, and directly moving the dental casts upon movement. Links 152 are disposed between the sliding assembly 151, the joint assembly 153 and the dental cast resting assembly 154 to link the assemblies 151, 153 and 154 together. Therefore, the object of fixing or moving the dental casts can be achieved by tightening or loosening the screws of the dental cast adjusting structure 15, thereby eliminating the use of the soft wax and the instability caused by manually moving the dental casts.

The above-mentioned sphere 158 is connected with a metal frame and the dental cast is accommodated in the receptacle 159. To be noted, in practice, the connection between the dental cast and the dental cast adjusting structure 15 is not limited to the above-mentioned configuration. For example, in other embodiments, the metal frame can be replaced by other simpler structures such as rod, cylinder, sheet, or plate. In more specific, before adjusting the position of the dental cast, any of the mentioned structures is inserted into the corresponding hole or recess on the dental cast for fixing the connection. Then, the adjusting structure 15 is moved or adjusted to achieve the same function. No matter which adjusting structure is adopted, it is not to limit the invention.

Figure 4:
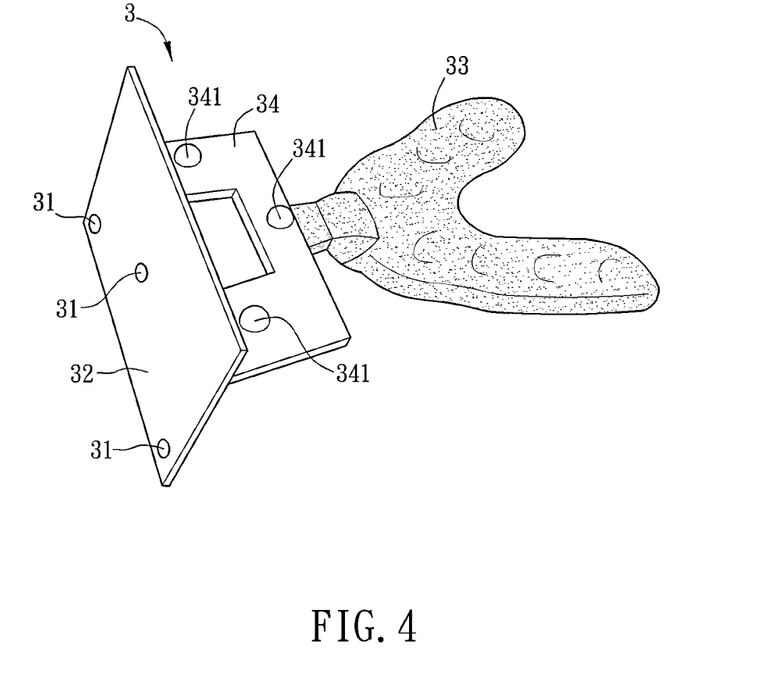
FIG. 4 is a schematic illustration showing the exterior of the label module in accordance with the embodiment of the invention.

FIG. 4 is a schematic illustration showing the exterior of the label module in accordance with the embodiment of the invention. The label module has at least a label. As shown in FIG. 4, the label module 3 in this aspect of the embodiment has three labels 31. However, the invention is not restricted thereto. Herein, the use of three labels 31 is only adapted to the active optical technique, and the three labels 31 are used to describe the spatial relationship of six degrees of freedom including three axial moving directions and three rotation directions thereof. Thus, in other embodiments when the detecting device adopts the ultrasonic or magnetic inductive technique, the label module 3 may correspondingly have one label 31.

In this embodiment, the labels 31 are disposed on a label carrying member 32 so that the relative position relationships therebetween can be fixed. In an aspect of this embodiment, the label 31 is a light-emitting diode (LED), preferably an infrared LED, more particularly an infrared LED packaged by way of surface mount technology (SMT). The label carrying member 32 may be a universal printed circuit board (PCB), or a plate material or a sheet material, which generally has wires or can provide the power. The labels 31 are not disposed on the same straight line. As shown in FIG. 4, the virtual connecting lines between the three labels 31 in this aspect of this embodiment certainly form a triangular serving as the reference of the subsequent calculation. The angles and the lengths of the sides of the triangular are not particularly restricted in this invention. To be noted, in other embodiments, when the detecting device 2 adopts the passive detecting technology, the labels 31 are, for example but not limited to, reflective members or recognizable special patterns (e.g. alternate black and white strips).

In addition, the label module 3 in this aspect of this embodiment may further have a bite member 33 and a positioning aid 34. The bite member 33 may be, for example, a bite sheet, a bite stent or the like. The positioning aid 34 may be a plastic sheet that has one end connected with the label carrying member 32, and the other end connected with the bite member 33. At least a reference object 341 is disposed on the positioning aid 34, and it does substantially not generate scattered light under X-ray photograph. In more specific, the reference object 341 may include, for example but without limitation to, a ceramic bead or an object, which can be recognized under the X ray, and cannot generate the scattered image during the computed tomography (CT) process, for example. In the aspect of this embodiment, the positioning aid 34 has three reference objects 341, which are not disposed on the same straight line, wherein the virtual connecting lines between the reference objects 341 can form a triangular. When this label module 3 of this aspect is utilized, the patient or the person requiring the orthodontic or orthognathic surgery can bite the bite member 33 before the surgery and the CT is performed. Since the reference objects 341 can be recognized on the CT image and the relative positions between the bite member 33, the reference objects 341 and the labels 31 are fixed, the relative spatial position transforming relationships between the reference objects 341 and the labels 31 can be obtained.

Figure 5:
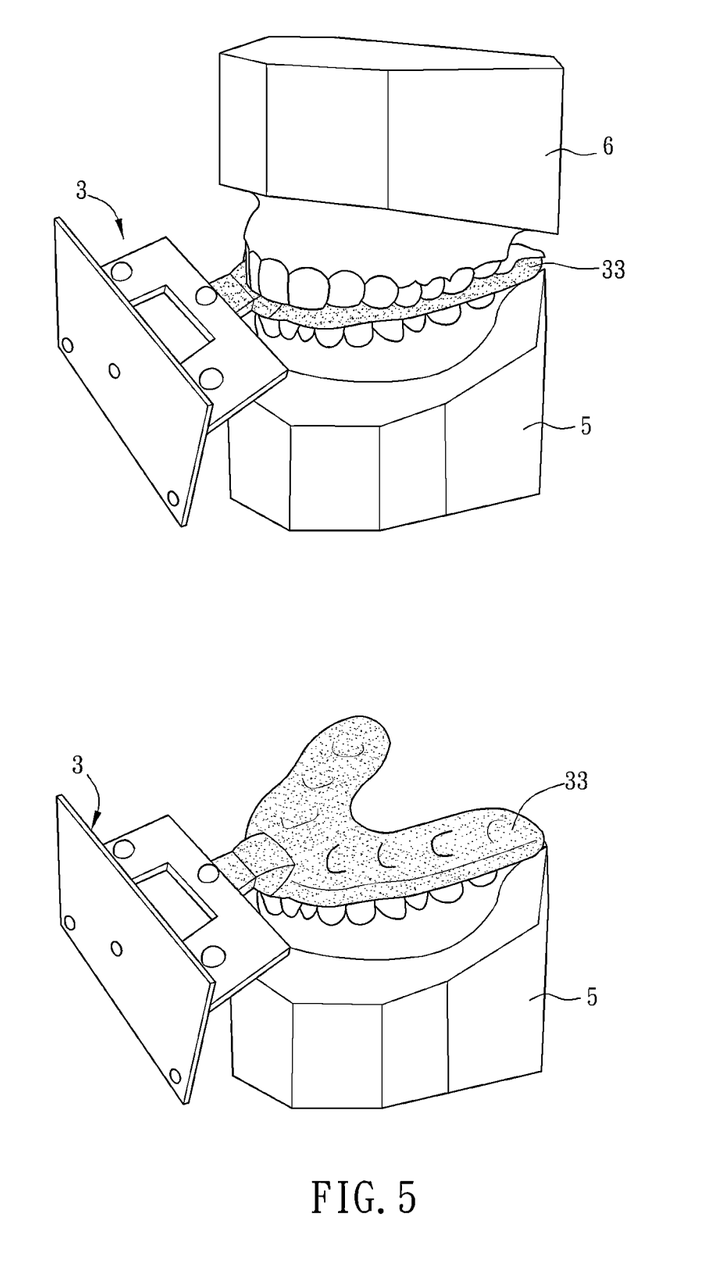
FIG. 5 is a schematic illustration showing a first/second dental cast combined with a label module in accordance with an aspect of the embodiment of the invention.

The disposed position of the label module 3 will be further described hereinafter. FIG. 5 is a schematic illustration showing a first/second dental cast combined with a label module in accordance with an aspect of the embodiment of the invention. When the planning system has a label module 3, the label module 3 is disposed on the first dental cast 5. For example, the bite member 35 is disposed on a first dental cast 5 (mandible dental cast), or a second dental cast 6 (palate dental cast) and the first dental cast 5 (mandible dental cast) tightly bite the bite member 35. According to the mounting method of the invention, the first dental cast 5 and the second dental cast 6 are connected to the label module 3' at different periods.

As shown in FIG. 1A, the data processing device 4 of this embodiment has a processing unit 41 and a storage unit 42. The data processing device 4 is signally connected with the detecting device 2 and stores the midface and mandible image data 421 in the storage unit 42. The midface and mandible image data 421 may include, for example but without limitation to, the image of human teeth, preferably includes the teeth images of the palate and mandible of the human, and more preferably includes the images of the palate and mandible teeth and the facial jawbone. The invention is not particularly restricted thereto. In addition, the data processing device 4 may be signally connected with the detecting device 2 in a wired or wireless manner to receive and process the traced data.

Figure 6:
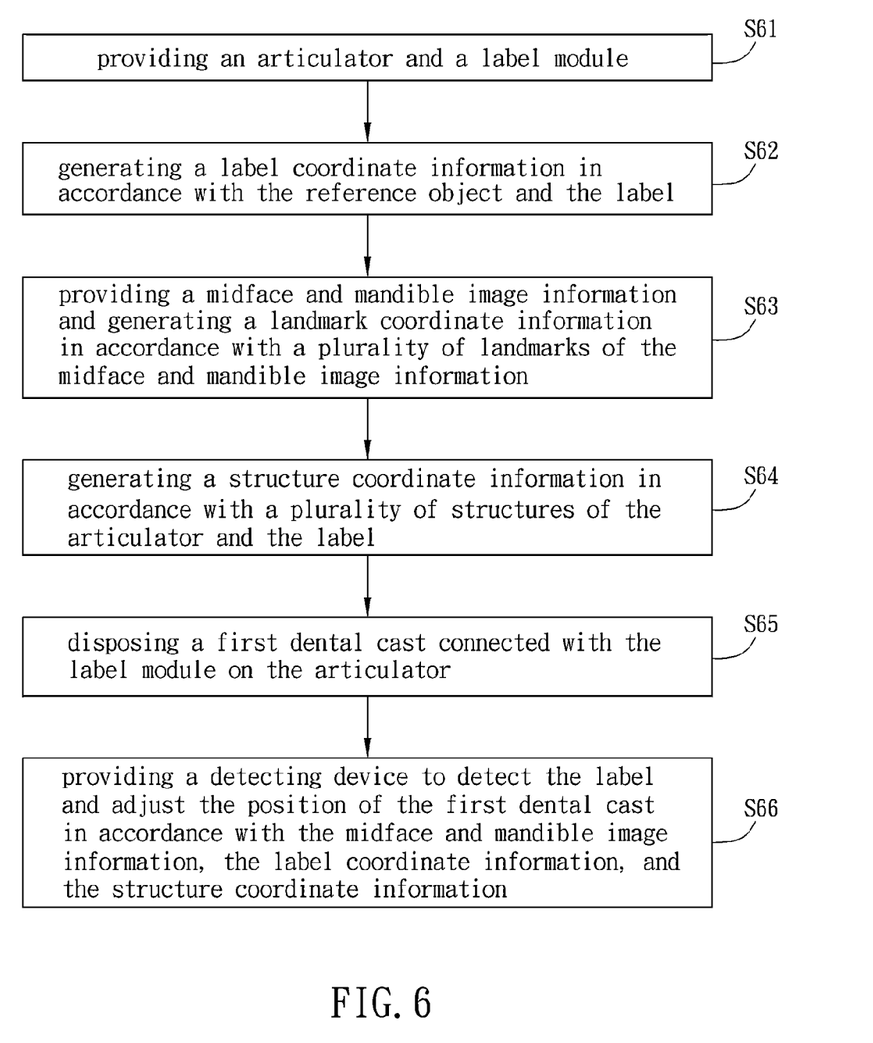
FIG. 6 is a flow chart of a mounting method of dental cast in accordance with the embodiment of the invention.

FIG. 6 is a flow chart showing steps of a mounting method of dental cast according to the embodiment of the invention. The mounting method of the invention will be described with reference to the above-mentioned planning system. To be noted, the mounting method of dental cast is applied with, for example but not limited to, the above articulator. In practice, it is also possible to be applied with the conventional or other types of articulators.

Moreover, it is noted that the midface and mandible image data of the patient may be established and stored in advance before mounting the dental cast. In this embodiment, the patient bites the label module 3 having the bite member 34 (see FIG. 4B), and then the CT is performed to obtain and store the midface and mandible image data to the storage unit of the data processing device. Preferably, the midface and mandible image data may represent the image models of the three-dimensional facial jawbone and the maxilla and mandible.

Referring to FIG. 6, in the step S61, an articulator and a label module are provided. Herein, the label module has at least a label and at least a reference object. The related contents and technical features of this step are all illustrated in the above embodiment, so the detailed descriptions will be omitted.

Then, the step S62 is to generate a label coordinate information in accordance with the reference object and the label. In more detailed, as shown in FIG. 4, the label coordinate information is generated by detecting and recording the coordinate relationship between the reference object 341 and the label 31. Herein, the label coordinate information is recorded in the storage unit of the data processing device.

The step S63 is to provide a midface and mandible image information and generating a landmark coordinate information in accordance with a plurality of landmarks of the midface and mandible image information. In this step S63, the data processing device is used to calculate the relative relationship between the landmarks of patient according to the midface and mandible image information, and then records the calculated results to generate the desired landmark coordinate information. The landmarks include left and right condyles, upper edges of left and right auditory meatuses, lower edge of orbital bone and/or the reference objects. Preferably, the left and right condyles are the inner points of left and right condyles. In order to increase the accuracy of the mounting method of dental cast, the articulator can be adjusted according to the obtained relative relationship in advance before the mounting step. For example, as shown in FIG. 2A, the distance between two position indicators 119 of the articulator 1 may be adjusted to be constant in accordance with the distance between the inner points of the left and right condyles.

Referring to FIG. 6, the step S64 is to generate a structure coordinate information in accordance with a plurality of structures of the articulator and the label. As shown in FIGS. 2A and 4, the structure coordinate data is obtained by detecting and recording the relative coordinate relationships between a plurality of structures of the articulator 1 and the labels 31 of the label module 3. The above-mentioned structures may include, for example but without limitation to, the upper arm portion 121, the pivot shaft 122 and/or the two position indicators 119. Preferably, the pivot shaft 122 is a shaft of the upper arm portion 121. The detecting method includes, for example but not limited to, referring to the pointing direction of the probe applied in the detecting device so as to directly determine the shaft of the pivot shaft 122.

The step S65 is to dispose a first dental cast connected with the label module on the articulator. The first dental cast is preferably a mandible dental cast manufactured according to the teeth of the patient or the person requiring the orthodontic or orthognathic surgery. The label module is, for example, the label module 3 of FIG. 4. The connection between the first dental cast and the label module is shown as FIG. 5. The material of the first dental cast includes, for example but not limited to, plaster. After connecting the label module to the first dental cast, the first dental cast is disposed on the lower alignment member of the articulator by embedding and screwing.

After the three sets of information are obtained, the detecting device traces the label of the label module disposed on the first dental cast (step S66). Next, the data processing device displays an image on a screen in accordance with the midface and mandible image information, the label coordinate information, and the structure coordinate information, so that the operator or doctor can adjust the position of the first dental cast with respect to the articulator.

In more specific, in one aspect of this embodiment, the data processing device is utilized to load the above-mentioned landmark coordinate information, label coordinate information and structure coordinate information. The landmark coordinate information includes, for example, the coordinate transfer relationships between the inner points of the left and right condyles and the reference objects in the midface and mandible image data; the structure coordinate information includes, for example, the coordinate transfer relationships between the labels of the label module and the pivot shaft, the position indicator and the upper arm portion of the articulator, respectively; and the label coordinate information includes, for example, the coordinate transfer relationships between the reference objects of the label module and the labels of the label module.

Figure 7A:
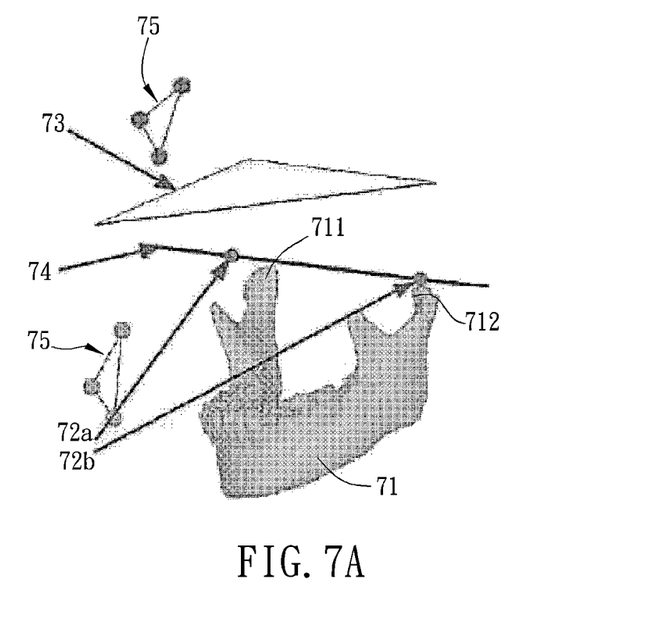
FIG. 7A is a schematic illustration showing an image obtained when mounting the first dental cast.

After the three sets of information are integrated, the image data established by the CT can be combined with the traced results. Accordingly, the relative coordinate position relationship between the mandible image and the articulator can be calculated and shown in FIG. 7A by similarly utilizing the data processing device to load the mandible image data in the midface and mandible image data and combine with the positions of the labels immediately traced by the detecting device. FIG. 7A is a schematic illustration showing an image obtained when the first dental cast is mounted in accordance with the embodiment of the invention. As shown in FIG. 7A, the portions, which are computed by combining the three sets of information with the traced results of the detecting device and then displayed on the screen, may include the mandible image 71, position indicator images 72a and 72b, upper arm portion image 73, pivot shaft image 74, and label images 75.

Therefore, the operator or doctor can move the first dental cast through the manual or automatic instrument to make condyle inner point images 711 and 712 of the mandible image 71 be overlapped with the positions of the position indicator images 72a and 72b, respectively. After the overlap is completed, it represents that the mounting procedure of the first dental cast is completed.

After the mounting procedure of the first dental cast, the mounting method of the invention is continue to mount the second dental cast, which is a palate dental cast.

Figure 7B:
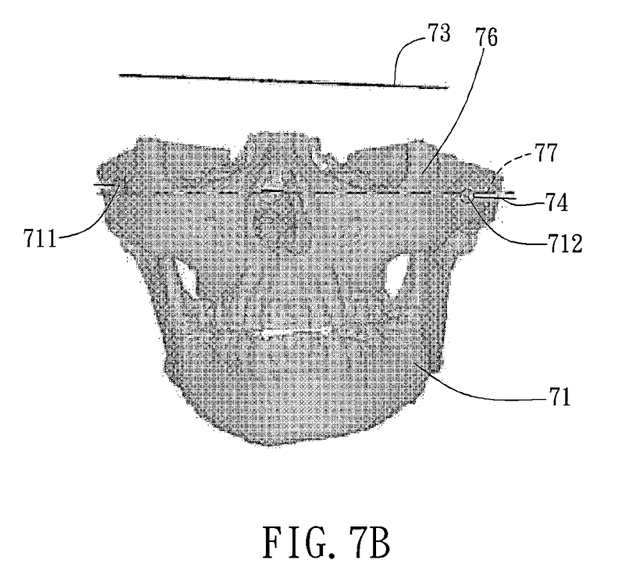
FIG. 7B is a schematic illustration showing an image obtained when mounting the second dental cast.

In the aspect of this embodiment, after the mounting procedure of the first dental cast, the label module originally disposed on the first dental cast is interposed between the first dental cast and the second dental cast. Thereafter, the labels of the label module are similarly traced by the detecting device, and the three sets of information are combined so that the results can be displayed on the screen, as shown in FIG. 7B. Herein, FIG. 7B is a schematic illustration showing an image obtained when the second dental cast is mounted in accordance with the embodiment of the invention. The image contents include the maxilla and at least a portion of maxillofacial bone image 76 of the patient, and the FH plane image 77 and the upper arm portion image 73 defined by the data processing device in accordance with the image data. Thus, the operator or doctor can utilize the manual or automatic instrument to rotate the upper arm portion of the articulator until the FH plane image 77 is parallel with the upper arm portion image 73, and then fixes the second dental cast to the upper alignment member 14 (see FIG. 2A) to complete the mounting procedure.

It is to be specified that although various articulators have the little structural differences, the mounting method of dental cast of the invention is constructed based on the tracing technique in conjunction with the CT imaging technique. Even if the used articulator is different from the structure of the above-mentioned articulator, any combination is still deemed as falling within the scope of the invention as long as the same effect can be achieved.

In summary, the mounting method of dental cast of the invention generates the label coordinate information, the landmark coordinate information, and the structure coordinate information for transferring the detecting results into images. Thus, when the detecting device detects the label to trace the position variations of the dental cast with respect to the articulator, it is possible to present the three-dimensional image model of facial jawbone by using the data processing device to combine the generated information with the midface and mandible image data. Accordingly, the operator or doctor can view the three-dimensional image model to avoid the blind spots. Moreover, the mounting method of the invention can quantify the relationship of special coordinates between the dental cast and the articulator, which can be simply applied to auxiliary calculating software for providing the necessary reference information. Furthermore, since the relative relationship between all objects is determined, it is possible to label the correct mounting location in the image, which is used as the direction and distance references for moving the dental cast. This feature can achieve the desired effect of real-time adjustment.

Compared with the conventional art, the mounting method of dental cast of the invention utilizes the detecting technology to replace the conventional face bow, so that it is possible to trace the difference between the relative relationship of the dental cast and the articulator and the real situation of the patient in real time. Thus, the invention is advantageous in data quantification. Besides, the established image can rapidly and precisely guide the operator or doctor to dispose the dental cast on the proper location. As a result, the present invention can efficiently enhance the reliability of the orthodontics and orthognathic planning.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A mounting method of dental cast performed by a planning system, the planning system includes an articulator, a detecting device, at least a label module and a data processing device the detecting device is disposed in correspondence with the articulator, the data processing device is signally connected with the detecting device and stores at least one midface and mandible image information, the detecting device detects or sense the label module, the label module has at least a label member, reference objects, a bite member, a positioning aid member and a label carrying the member, the positioning aid member has the reference objects, and the positioning aid member is connected with the bite member and the label carrying member, respectively, and the label member is fixed to the label carrying member, the method comprising the steps of:

generating a label coordinate information in accordance with the reference objects and the label member by the data processing device;

generating a landmark coordinate information in accordance with a plurality of landmarks of the midface and mandible image information by the data processing device;

generating a structure coordinate information by detecting and recording the relative coordinate relationships between a plurality of structures of the articulator and the label member of the label module by the detecting device;

disposing a first dental cast connected with the label module on the articulator; and detecting the label member and adjusting the position of the first dental cast in accordance with the midface and mandible image information, the label coordinate information, and the structure coordinate information to complete mounting procedure.

2. The method according to claim 1, wherein the landmarks comprises condyle, upper edge of auditory meatus, lower edges of orbital bones and/or the reference objects.

3. The method according to claim 1, wherein the structures of the articulator comprise an upper arm portion, a pivot shaft and/or two position indicators of the articulator.

4. The method according to claim 3, wherein one of the structures of the articulator is a center of the pivot shaft.

5. The method according to claim 1, wherein the step of generating the structure coordinate information is to detect the structures and the label member by the detecting device.

6. The method according to claim 1, wherein the first dental cast is a mandible dental cast.

7. The method according to claim 6, further comprising the steps of:
   providing a second dental cast, wherein the label member is disposed between the first dental cast and the second dental cast; and
   adjusting the position of the second dental cast in accordance with the midface and mandible image information, the label coordinate information, and the structure coordinate information.

8. The method according to claim 7, wherein the second dental cast is a palate dental cast.

9. The method according to claim 1, wherein the detecting device is an optical, mechanical, ultrasonic, gyroscope or magnetic inductive detecting device.

10. The method according to claim 9, wherein the detecting device is an optical detecting device and comprises two photographing modules, and the label member is a light-emitting diode (LED), a pattern or a reflective member.

* * * * *